(12) United States Patent
Kawachi (10) Patent No.: US 9,204,936 B2
(45) Date of Patent: Dec. 8, 2015

(54) ENDOSCOPE CLEANING/DISINFECTING APPARATUS

(71) Applicant: OLYMPUS MEDICAL SYSTEMS CORP., Tokyo (JP)

(72) Inventor: Shinichiro Kawachi, Inagi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/333,913

(22) Filed: Jul. 17, 2014

(65) Prior Publication Data

US 2014/0326282 A1  Nov. 6, 2014

Related U.S. Application Data

(63) Continuation of application No. PCT/JP2013/082799, filed on Dec. 6, 2013.

(30) Foreign Application Priority Data

Feb. 13, 2013 (JP) ................................. 2013-025873

(51) Int. Cl.
 *A61B 19/00* (2006.01)
 *A61B 1/12* (2006.01)
(52) U.S. Cl.
 CPC ................. *A61B 19/34* (2013.01); *A61B 1/121* (2013.01); *A61B 2019/343* (2013.01)
(58) Field of Classification Search
 USPC ................................................. 134/94.1, 99.1
 See application file for complete search history.

(56) References Cited

U.S. PATENT DOCUMENTS

| | | | |
|---|---|---|---|
| 5,558,841 | A | 9/1996 | Nakagawa et al. |
| 5,932,171 | A | 8/1999 | Malchesky |
| 6,558,620 | B1 | 5/2003 | Sanford et al. |
| 6,585,943 | B1 | 7/2003 | Sanford et al. |
| 2002/0001537 | A1 | 1/2002 | Hlebovy et al. |
| 2003/0121532 | A1* | 7/2003 | Coughlin et al. ................. 134/7 |
| 2003/0190256 | A1* | 10/2003 | Halstead et al. ................ 422/28 |
| 2003/0190257 | A1* | 10/2003 | Halstead et al. ................ 422/28 |

(Continued)

FOREIGN PATENT DOCUMENTS

| | | |
|---|---|---|
| JP | 59-32435 A | 2/1984 |
| JP | 07-008456 A | 1/1995 |
| JP | 2001-514932 A | 9/2001 |
| JP | 2002-034915 A | 2/2002 |

(Continued)

*Primary Examiner* — Michael Barr
*Assistant Examiner* — Benjamin L Osterhout
(74) *Attorney, Agent, or Firm* — Scully, Scott, Murphy & Presser, PC (57) ABSTRACT

An endoscope cleaning/disinfecting apparatus has a cleaning tank in which an endoscope is disposed, a chemical tank that stores a chemical solution, a water supply connecting portion that is connectable to a water service pipe, an endoscope cleaning/disinfecting section having a first conduit that connects the cleaning tank and the chemical tank, and a second conduit that connects the cleaning tank and the water supply connecting portion, an operation panel that is a water information input section to which hardness information of water that is supplied from the water service pipe is inputted, a memory that is a history information retaining section that retains cleaning history information of the endoscope cleaning/disinfecting section, and a control section that is a determination section that determines necessity or nonnecessity of scale removal of the endoscope cleaning/disinfecting section based on the hardness information and the cleaning history information.

6 Claims, 8 Drawing Sheets

(56) References Cited

U.S. PATENT DOCUMENTS

| | | |
|---|---|---|
| 2004/0007255 A1* | 1/2004 | Labib et al. ............... 134/30 |
| 2009/0065034 A1* | 3/2009 | Suzuki et al. ............. 134/56 R |
| 2010/0202920 A1* | 8/2010 | Otte et al. ................. 422/28 |
| 2010/0252074 A1* | 10/2010 | Sewake et al. ............. 134/19 |
| 2011/0097248 A1* | 4/2011 | Tomita et al. ............. 422/292 |

FOREIGN PATENT DOCUMENTS

| | | |
|---|---|---|
| JP | 2002-045334 A | 2/2002 |
| JP | 2003-010115 A | 1/2003 |
| JP | 2003-521345 A | 7/2003 |
| WO | WO 99/08719 A2 | 2/1999 |
| WO | WO 01/56615 A2 | 8/2001 |

* cited by examiner

| HARDNESS (W,H) / PH | 0~80 | 80~200 | 200~400 | 400 OR MORE |
|---|---|---|---|---|
| 0~3 | 260 TIMES | ... | ... | 40 TIMES |
| 3~6 | : | : | : | : |
| 6~8 | : | : | : | : |
| 8~11 | : | : | : | : |
| 11 OR MORE | 40 TIMES | ... | ... | 10 TIMES |

ENDOSCOPE CLEANING/DISINFECTING APPARATUS

CROSS REFERENCE TO RELATED APPLICATION

This application is a continuation application of PCT/JP2013/082799 filed on Dec. 6, 2013 and claims benefit of Japanese Application No. 2013-025873 filed in Japan on Feb. 13, 2013, the entire contents of which are incorporated herein by this reference.

BACKGROUND OF THE INVENTION

1. Field of the Invention

The present invention relates to an endoscope cleaning/disinfecting apparatus in which liquids such as tap water, a cleaning liquid and a disinfectant solution are supplied to an inside of the apparatus in order to perform cleaning, disinfection, rinse and the like of an endoscope.

2. Description of the Related Art

Conventionally, endoscopes have been widely used in a medical field and the like. Endoscopes that are used in the medical field are used by the insertion portions being inserted into bodies especially with the objectives of inspection and treatment, and therefore require cleaning and disinfection to be used again, after use. Cleaning and disinfection of the endoscopes which are already used are performed by known endoscope cleaning/disinfecting apparatuses.

In an endoscope cleaning/disinfecting apparatus as above, in order to perform cleaning, disinfection, rinse and the like of an endoscope that is already used, liquids such as tap water, a cleaning liquid and a disinfectant solution are supplied to the inside of the apparatus, and the liquids are circulated in the apparatus. The endoscope cleaning/disinfecting apparatus performs a drying step of drying the endoscope after completion of cleaning, disinfecting and rinsing steps for the endoscope.

Therefore, when an endoscope cleaning/disinfecting apparatus performs a series of steps such as cleaning, disinfecting and rinsing steps, and a drying step as above over a long period of time, calcium carbonate and magnesium carbonate sometimes form scale to adhere to the inside of a cleaning tank and insides of respective conduits that are provided in the endoscope cleaning/disinfecting apparatus, depending on the degree of the hardness of the tap water that is used.

Thus, the endoscope cleaning apparatus for removing the scale adhering to the inside of the cleaning apparatus and the like is disclosed in Japanese Patent Application Laid-Open Publication No. 2003-10115, for example.

The endoscope cleaning apparatus described in Japanese Patent Application Laid-Open Publication No. 2003-10115 has an electrolysis tank that can generate alkaline water and acid water by electrolysis, and an alkaline water tank and an acid water tank that can supply and store the respective alkaline water and acid water generated by the electrolysis tank, and is configured to supply acid water from at least one of the electrolysis tank and the acid water tank temporarily to the alkaline water tank to dissolve the scale adhering to the whole or part of the inside of the alkaline water tank.

SUMMARY OF THE INVENTION

An endoscope cleaning/disinfecting apparatus of one aspect of the present invention has a cleaning tank in which an endoscope is disposed, a storage section that stores a chemical solution, a water supply connecting portion that is connectable to a water service pipe, an endoscope cleaning/disinfecting section having a first conduit that connects the cleaning tank and the storage section, and a second conduit that connects the cleaning tank and the water supply connecting portion, a water information input section to which hardness information of water that is supplied from the water service pipe is inputted, a history information retaining section that retains cleaning history information of the endoscope cleaning/disinfecting section, and a determination section that determines necessity or nonnecessity of scale removal of the endoscope cleaning/disinfecting section based on the hardness information and the cleaning history information.

DETAILED DESCRIPTION OF THE PREFERRED EMBODIMENT

Hereinafter, an embodiment of the present invention will be described in detail with reference to the drawings.

Figure 1:
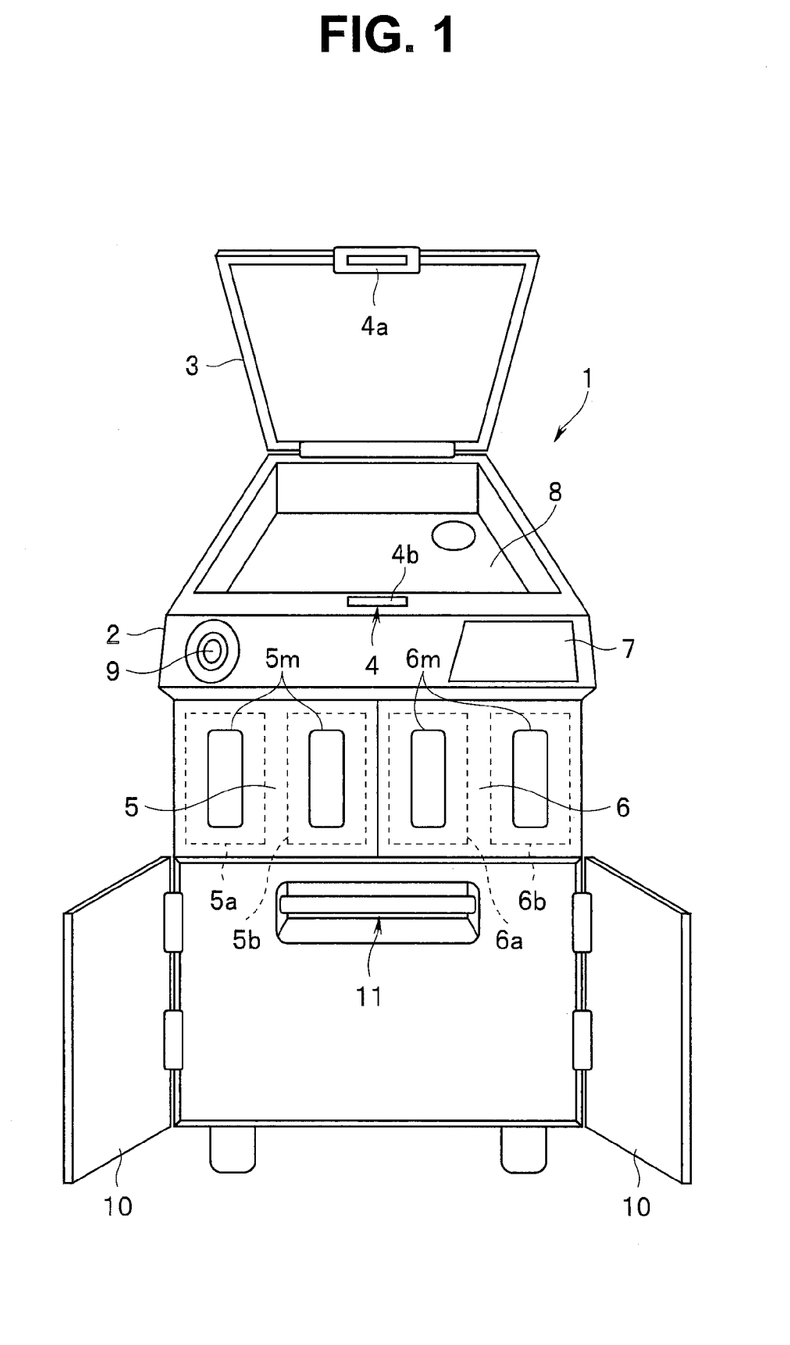
FIG. 1 is a perspective view that shows an exterior configuration of an entire endoscope cleaning/disinfecting apparatus according to one embodiment of the present invention, and shows a state in which a lid portion is opened.

FIG. 1 is a perspective view that shows an exterior configuration of an entire endoscope cleaning/disinfecting apparatus according to one embodiment of the present invention, and shows a state in which a lid portion is opened.

As shown in FIG. 1, an endoscope cleaning/disinfecting apparatus 1 of the present embodiment has an apparatus main body 2, and a top cover 3 that is a lid portion connected to the apparatus main body 2 to be openable and closable, and is configured to have an endoscope that is already used (not illustrated) accommodated and disposed therein, and clean and disinfect the endoscope by a cleaning and disinfecting step.

When the top cover 3 is closed, the top cover 3 is locked by a latch portion 4, and the apparatus main body 2 is hermetically sealed to be watertight.

For example, in a left half of a front surface of the apparatus main body 2, a cleaning agent/alcohol tray 5 is placed to be capable of being drawn forward of the apparatus main body 2. The cleaning agent/alcohol tray 5 accommodates a cleaning agent tank 5a that stores a cleaning agent that is a liquid to be used when an endoscope is cleaned, and an alcohol tank 5b that stores alcohol that is a liquid to be used when the endoscope after cleaning and disinfection is dried. The configuration capable of the cleaning agent/alcohol tray 5 being drawn enables the respective tanks 5a and 5b to be replaced, or the respective tanks 5a and 5b to be replenished with liquids.

Note that the cleaning agent/alcohol tray 5 is provided with two window portions 5m, and by the two window portions 5m, a user can confirm residual amounts of the cleaning agent and alcohol that are poured into the respective tanks 5a and 5b. The cleaning agent is a concentrated cleaning agent to be diluted to a predetermined concentration by tap water that is subjected to sterilizing processing by a supply water filter.

Further, for example, in a right half of the front surface of the apparatus main body 2, a disinfectant solution bottle tray 6 is placed to be capable of being drawn forward of the apparatus main body 2. The disinfectant solution bottle tray 6 accommodates a disinfectant solution bottle 6a in which a disinfectant solution such as peracetic acid that is a liquid to be used when an endoscope is disinfected is poured, and a buffering agent bottle 6b in which a buffering agent for the disinfectant solution is poured.

Note that the disinfectant solution bottle tray 6 also can accommodate a scale removal agent bottle 6x in which a scale removal agent, which will be described later, is poured, in juxtaposition with the disinfectant solution bottle 6a or in place with the disinfectant solution bottle 6a, at a time of execution of a scale removable program which will be described later.

Figure 2:
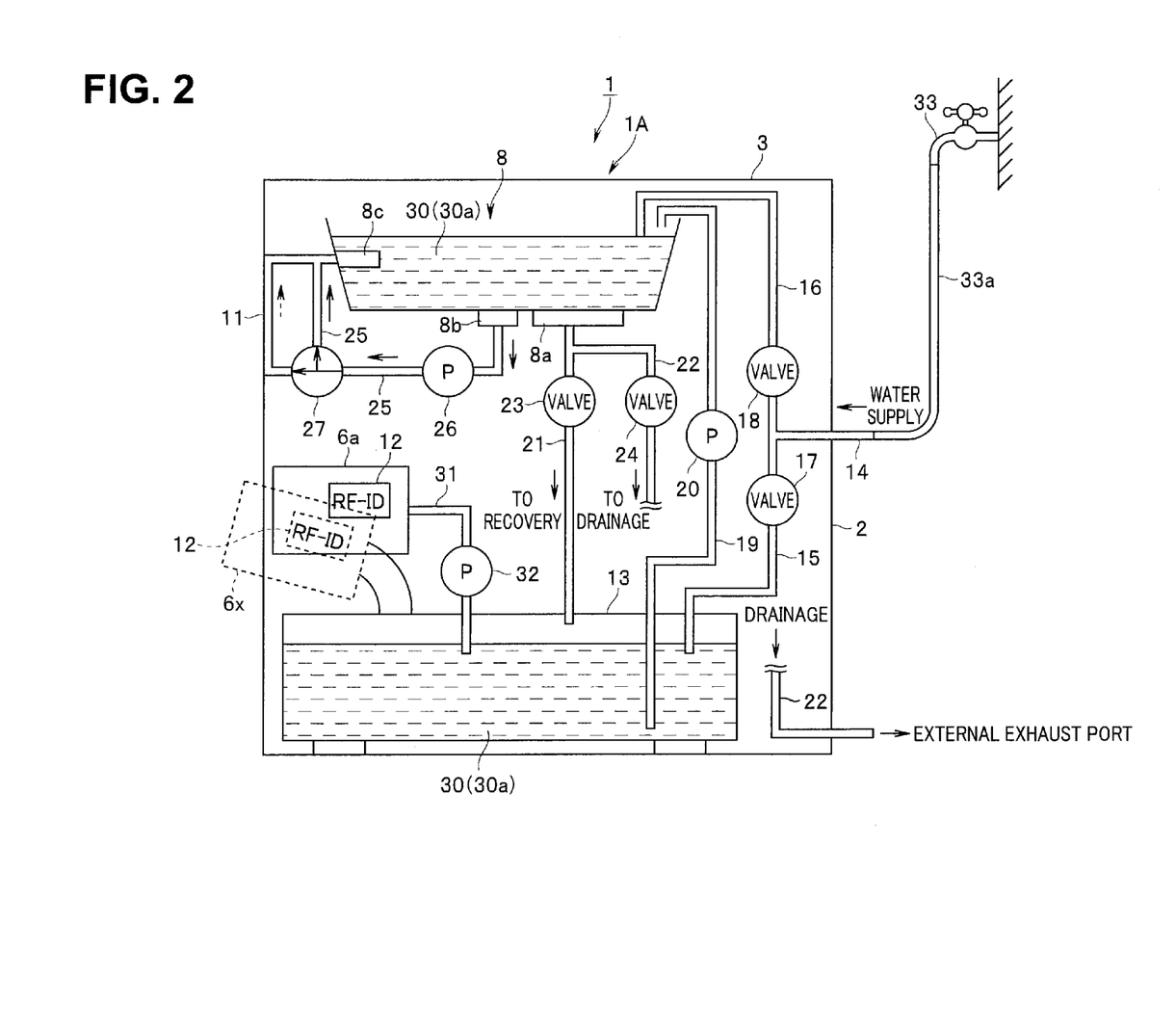
FIG. 2 is a diagram for explaining a conduit configuration of an inside of the endoscope cleaning/disinfecting apparatus shown in FIG. 1.

The configuration that is capable of the disinfectant solution bottle tray 6 being drawn enables the respective bottles 6a (or 6x) and 6b to be set, or enables the scale removal agent bottle 6x to be tilted by hand as shown in FIG. 2 to inject a chemical solution that is a scale removal agent into a chemical tank 13 which will be described later at the time of execution of the scale removal program.

Note that the disinfectant solution bottle tray 6 is provided with two window portions 6m, and by the two window portions 6m, residual amounts of the disinfectant solution and the buffering agent that are poured in the respective bottles 6a and 6b can be confirmed by the user.

Further, an operation panel 7 that includes a cleaning and disinfecting operation start switch for the apparatus main body 2, setting switches such as a cleaning and disinfecting mode selection switch is provided at an upper portion from the disinfectant solution bottle tray 6, on the front surface of the apparatus main body 2.

The operation panel 7 is a touch panel, for example, and can be used as an input section where hardness information of tap water and the like are inputted, besides the setting switches.

Note that the operation panel 7 can be configured by a touch panel of any one method of an optical method, a resistive membrane method and a capacitive method, and can include functions of display of various setting switches and as an input section where the hardness information or the like of tap water or the like is inputted. Further, the operation panel 7 may be configured as an operation switch that is configured as various setting switches and the input portion by having a plurality of buttons, instead of the touch panel.

Note that under normal conditions, the endoscope cleaning/disinfecting apparatus 1 performs an action according to a cleaning/disinfection program that is set in advance, when the endoscope cleaning/disinfecting apparatus 1 cleans/disinfects an endoscope by an operation of the operation panel 7. In the cleaning/disinfection program, the user can optionally set a cleaning time, a disinfecting time and the like, and when the user performs the setting, the user performs the setting by the various switches on the operation panel 7.

Further, in a substantially central portion on a top surface of the apparatus main body 2, a cleaning/disinfecting tank 8 (hereinafter, simply described as a cleaning tank 8) capable of accommodating an endoscope is provided. An endoscope accommodation port of the cleaning tank 8 which is a storage tank is covered with the top cover 3 as the openable and closable top cover 3 is closed at a time of cleaning and disinfection of an endoscope. Alternatively, at a time of execution of the scale removable program, the openable and closable top cover 3 is opened, and in a state in which an electromagnetic valve 23 is opened, and an electromagnetic valve 24 is closed, the scale removal agent bottle 6x is opened and the removal agent is poured into the cleaning/disinfecting tank 8 by a manual operation, whereby the chemical solution which is the scale removal agent can be injected into the chemical tank 13.

Further, an RF-ID receiving section 9 for transmitting and receiving information by radio with an RF-ID (a high-frequency automatic identification system: radio frequency identification) tag 12 that is an IC tag provided at the disinfectant solution bottle 6a is provided at an upper portion from the cleaning agent/alcohol tray 5, on the front surface of the apparatus main body 2.

The RF-ID tag 12 is provided on a top surface or a side surface of the disinfectant solution bottle 6a, for example, and the RF-ID tag 12 is moved close to the RF-ID receiving section 9, whereby information can be transmitted and received to and from the RF-ID tag 12 and the RF-ID receiving section 9.

Inside the RF-ID tag 12, related information including an identification code that identifies a disinfectant solution, an expiration date of the disinfectant solution, a lot number of the disinfectant solution, and a hydrogen ion exponent pH (potential hydrogen, power of hydrogen) indicating the degree of acidity and alkalinity of the disinfectant solution is recorded.

Further, a front door 10 is provided at a lower portion of the front surface of the apparatus main body 2. The front door 10 can be opened and closed without a tool, and when the front door 10 is opened, a scale detecting bypass conduit 11 that is placed on the front surface of the apparatus main body 2 is exposed.

The scale detecting bypass conduit 11, which will be described later, is a bypass conduit that is connected to a conduit in the endoscope cleaning/disinfecting apparatus 1. The scale detecting bypass conduit 11 is configured by using a transparent conduit member, for example, and the scale detecting bypass conduit 11 is connected to the conduit in the endoscope cleaning/disinfecting apparatus 1, whereby the user can visually recognize and detect an adhering state of scale in the conduit similarly to the conduits in the endoscope cleaning/disinfecting apparatus 1.

Next, a conduit configuration in the inside of the endoscope cleaning/disinfecting apparatus 1 of the present embodiment will be described with use of FIG. 2. FIG. 2 is a diagram for explaining the conduit configuration in the inside of the endoscope cleaning/disinfecting apparatus shown in FIG. 1.

As shown in FIG. 2, the endoscope cleaning/disinfecting apparatus 1 has an endoscope cleaning/disinfecting section 1A, and the endoscope cleaning/disinfecting section 1A is configured by having the cleaning tank 8, the chemical tank 13 that is the storage section which stores a chemical solution such as a disinfectant solution, a water supply connecting portion 14 that is connectable to a water supply faucet 33 connected to a water service pipe not illustrated, and a plurality of conduits 15, 16, 19, 22, 21 and 25. The respective conduits 15, 16, 19, 22, 21 and 25 are connected to at least one of the cleaning tank 8, the chemical tank 13 and the water supply connecting portion 14.

One end of a water supply hose 33a is connected to the water supply connecting portion 14. The other end of the water supply hose 33a is connected to the water supply faucet 33 at an outside, and tap water from the water supply faucet 33 is supplied to the water supply connecting portion 14. Note that the water supply connecting portion 14 may be configured to be connected to a water heater connected to the water service pipe not illustrated via the water supply hose 33a and supplied with hot water from the water heater.

The conduit 15 is a first conduit that connects the water supply connecting portion 14 and the chemical tank 13. Further, the conduit 16 is a second conduit that connects the water supply connecting portion 14 and the cleaning tank 8.

The disinfectant solution from the disinfectant solution bottle 6a is fed to the chemical tank 13 from a conduit 31 and a pump 32.

Further, tap water is fed to the chemical tank 13 via the first conduit 15 and an electromagnetic valve 17, and the disinfectant solution is diluted to a predetermined concentration. Further, a diluted disinfectant solution in the chemical tank 13, which is diluted to the predetermined concentration, is fed to the cleaning tank 8 via the conduit 19 and a pump 20.

Note that at a time of execution of the scale removal program which will be described later, from the scale removal agent bottle 6x in which a chemical solution 30a that is an acid solution of a predetermined pH value, for example, is poured, the chemical solution 30a is injected into the chemical tank 13 by hand, for example, as the scale removal agent.

As the acid chemical solution 30a, a citric acid aqueous solution, for example, is cited.

The scale removal agent bottle 6x is used at the time of execution of the scale removal program, and is prepared separately from the disinfectant solution bottle 6a. As for the scale removal agent bottle 6x, as described above, the chemical solution 30a may be injected into the chemical tank 13 by hand, or the scale removal agent bottle 6x may be set in place of the disinfectant solution bottle 6a which is set in the disinfectant solution bottle tray 6, and the chemical solution 30a is controlled to be injected into the chemical tank 13 via the conduit 31 by the pump 32 that configures a scale removal agent supply section. Alternatively, the openable and closable top cover 3 is opened, and in the state in which the electromagnetic valve 23 is opened and the electromagnetic valve 24 is closed, the scale removal agent bottle 6x is opened and the removal agent is poured into the cleaning and disinfecting tank 8 by a manual operation, whereby the chemical solution 30a may be injected into the chemical tank 13.

Tap water is fed to the cleaning tank 8 via the second conduit 16 and an electromagnetic valve 18, besides the diluted disinfectant solution 30 of the predetermined concentration or the chemical solution 30a, and the tap water is used in rinsing or the like after disinfection. Further, the cleaning tank 8 is connected to the chemical tank 13 via an exhaust port 8a, the conduit 21 and the electromagnetic valve 23, and the diluted disinfectant solution 30 or the chemical solution 30a after cleaning in the cleaning tank 8 is recovered into the chemical tank 13. Further, the cleaning tank 8 is connected to an exhaust port via the exhaust port 8a, the conduit 22 and the electromagnetic valve 24, and the diluted cleaning liquid, or the diluted disinfectant solution after cleaning in the cleaning tank 8, the tap water after rinsing and the like are discarded to the exhaust port outside the apparatus:

Further, the cleaning tank 8 is such that the diluted disinfectant solution 30, the chemical solution 30a or the diluted cleaning liquid, the tap water for rinsing and the like in the cleaning tank 8 are circulated via a circulation port 8b, the conduits 25 and 11, a branch portion 27, a pump 26 and a circulation nozzle 8c. In this case, the liquids that are circulated also flow into the scale detecting bypass conduit 11.

Note that the chemical tank 13 not only stores the disinfectant solution from the disinfectant solution bottle 6a, but also includes the function as the storage section that stores the chemical solution 30a that is the scale removal agent at the time of execution of the scale removal program which will be described later.

Further, the respective electromagnetic valves 17, 18, 23 and 24 and the pumps 20, 26 and 32 are provided with sensors such as flow meters (not illustrated), and a control section 52 that will be described later controls the electromagnetic valves 17, 18, 23 and 24, and the pumps 20, 26 and 32 based on the flow information from the flow meters, and thereby performs control of fluids that flow into the respective conduits.

The endoscope cleaning/disinfecting apparatus 1 of the present embodiment has the endoscope cleaning/disinfecting section 1A, the operation panel 7 which is a water information input section where the hardness information of the water that is supplied from the water service pipe is inputted, a memory 61 (described later) that is a history information retaining section that retains cleaning history information of the endoscope cleaning/disinfecting section 1A, and the control section 52 (described later) that is a determination section that determines necessity or nonnecessity of scale removal of the endoscope cleaning/disinfecting section 1A from the hardness information and the cleaning history information.

The endoscope cleaning/disinfecting apparatus 1 can determine necessity or nonnecessity of scale removal of the endoscope cleaning/disinfecting section 1A by including at least the above described constituent elements. When a result of the determination is that removal of the scale of the endoscope cleaning/disinfecting section 1A is determined as necessary, for example, the control section 52 causes a message to execute the scale removal program to be displayed on the operation panel 7. Thereby, notification of carrying out scale removal is performed.

Figure 3:
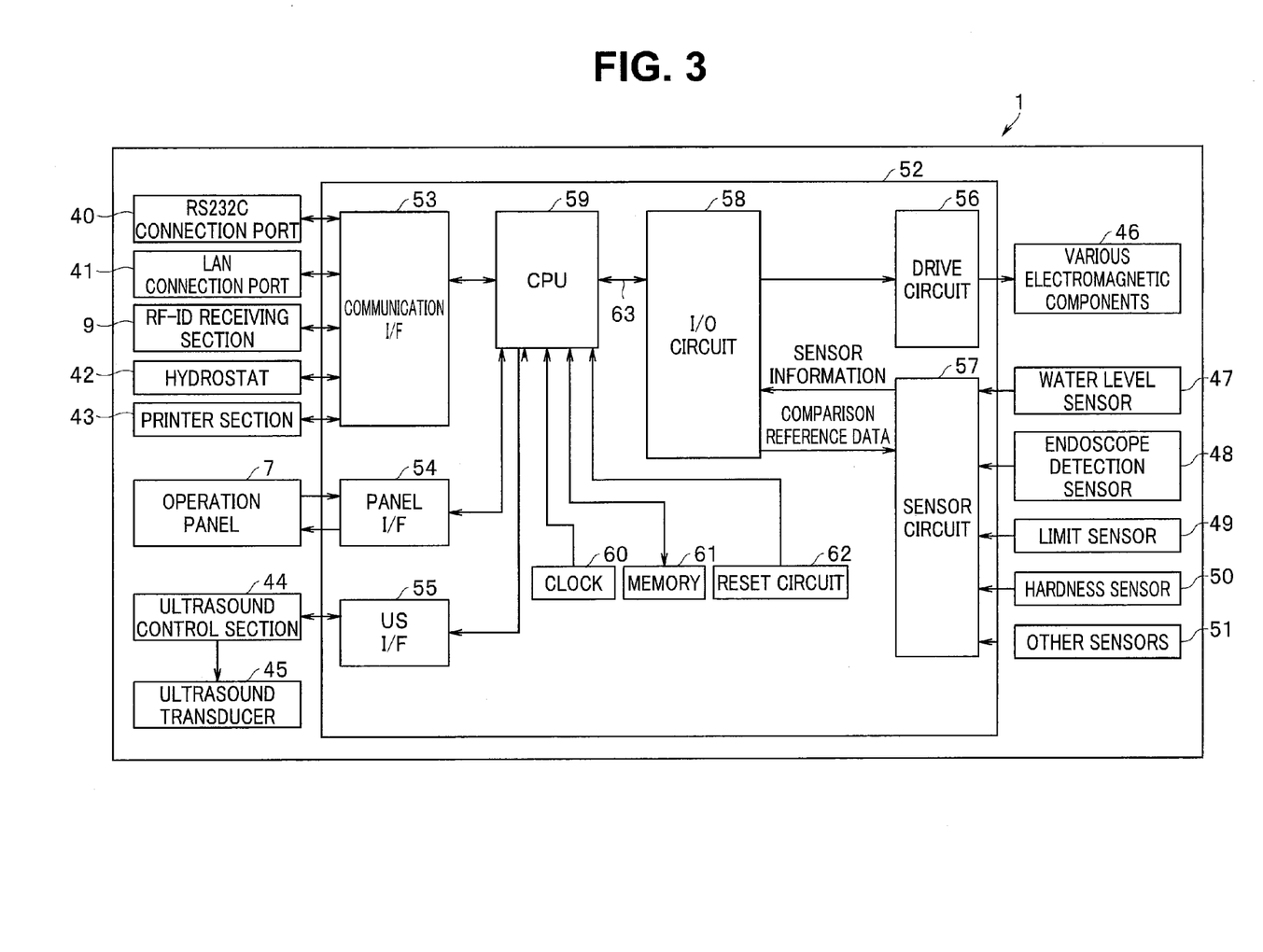
FIG. 3 is a block diagram showing a circuit configuration of the endoscope cleaning/disinfecting apparatus shown in FIG. 1.

A configuration of an electric circuit of the endoscope cleaning/disinfecting apparatus 1 as above will be described with use of FIG. 3. FIG. 3 is a block diagram showing a circuit configuration of the endoscope cleaning/disinfecting apparatus shown in FIG. 1. Note that in the circuit configuration of the endoscope cleaning/disinfecting apparatus 1 shown in FIG. 3, blocks of a main part of the present invention will be described in detail, and blocks of parts other than the main part will be briefly described since the blocks are known.

As shown in FIG. 3, the endoscope cleaning/disinfecting apparatus 1 has an RS232C connection port 40 and a LAN (local area network) connection port 41 and is externally communicable, and is provided with a water level sensor 47, an endoscope detection sensor 48, a limit sensor 49, a hardness sensor 50 and other sensors 51.

The RS232C connection port 40 connects to a personal computer (hereinafter, an outside PC) as an outside apparatus and the like to be capable of serial communication with the outside PC. The LAN connection port 41 connects to an in-hospital network or the like to be capable of communication.

Note that the water level sensor 47 detects levels of the diluted disinfectant solution 30 and the like stored in the cleaning tank 8, and the endoscope detection sensor 48 detects that an endoscope is disposed in the cleaning tank 8. Further, the limit sensor 49 detects an opening and closing state of the top cover 3 according to whether a latch protrusion portion 4a that is on a top cover 3 side and configures the latch portion 4 engages with a latch receiving portion 4b on an apparatus main body 2 side. Further, the hardness sensor 50 is provided in the second conduit 16 or the water supply connecting portion 14, for example, and detects the hardness of the tap water to be supplied.

Further, the endoscope cleaning/disinfecting apparatus. 1 is configured by having the RF-ID receiving section 9, a hydrostat 42, a printer section 43, the operation panel 7, an ultrasound transducer 45 that generates ultrasound, an ultrasound control section 44 that drives the ultrasound transducer 45, and various electromagnetic components 46 such as electromagnetic valves and pumps, and being provided with the control section 52 that controls the components.

The control section 52 has a communication interface (hereinafter, a communication I/F) 53 that performs communication with the RS232C connection port 40, the LAN connection port 41 and the like, a panel interface (hereinafter, a panel I/F) 54 that connects to the operation panel 7, and a US interface (hereinafter, a US I/F) 55 that connects to the ultrasound control section 44.

Furthermore, the control section 52 has a drive circuit 56 that drives the various electromagnetic components 46, a sensor circuit 57 that processes signals from the water level sensor 47 and the like, and an I/O circuit 58 that connects to the drive circuit 56 and the sensor circuit 57.

The control section 52 includes a CPU 59 as control means that controls the respective sections via the communication I/F 53, the panel I/F 54, the US I/F 55 and the I/O circuit 58. Namely, the CPU 59 is configured to control all the components of the endoscope cleaning/disinfecting apparatus 1. Note that the CPU 59 and the I/O circuit 58 are connected by a bus 63.

The CPU 59 is connected to a clock 60, a memory 61 and a reset circuit 62. The clock 60 outputs time information for controlling a cleaning and disinfecting step in terms of time and time information necessary to determine necessity or nonnecessity of scale removal which will be described later to the CPU 59.

Note that the CPU 59 has a wait counter (not illustrated) that counts up in accordance with a clock that is time information from the clock 60, and when the CPU 59 finishes a series of steps of the cleaning and disinfecting step and a dry step, for example, the CPU 59 controls the wait counter to count up in accordance with the clock, and updates a count value as cleaning and disinfection history information (hereinafter, simply called cleaning history information).

The memory 61 is a non-volatile memory that retains data thereof even if a power supply is turned off, and is configured to store a setting content with respect to the cleaning and disinfecting step, and the cleaning history information at the time of execution, endoscope information and user information, patient information, information concerning a kind of a disinfectant solution, hardness information of tap water, maintenance information such as an expiration date and the number of times of use of consumables such as a cleaning liquid, billing information, error support information and the like.

Further, the memory 61 stores map data (see FIG. 5) that shows a count value that is a threshold value that corresponds to the information concerning the kind of the disinfectant solution and the hardness information of the tap water, and is necessary to determine the scale removal time.

The reset circuit 62 monitors a voltage that is supplied from a power supply not illustrated, and resets the CPU 59 when the voltage is out of a prescribed value.

In the present embodiment, when the endoscope cleaning/ disinfecting apparatus 1 is installed in a hospital, the user inputs a country, an area or the like in which the user uses the apparatus main body 2 by using the operation panel 7 which is a water information input section. Thereupon, the CPU 59 acquires the hardness information of the tap water to be used from the hardness information table of water corresponding to the country or the area, which is stored in the memory 61, and controls the hardness information to be stored and set in the memory 61.

Further, in the present embodiment, before the disinfectant solution bottle 6a to be used in the endoscope cleaning/disinfecting apparatus 1 is set to the disinfectant solution bottle tray 6, the RF-ID tag 12 of the disinfectant solution bottle 6a is moved close to the RF-ID receiving section 9 of the apparatus main body 2, whereby the CPU 59 receives the information relating to the kind of the disinfectant solution of the disinfectant solution bottle 6a (the identification cord, a pH value and the like) by the RF-ID receiving section 9, and controls the received information relating to the kind of the disinfectant solution to be stored in the memory 61.

As above, in the present embodiment, before use of the endoscope cleaning/disinfecting apparatus 1, the hardness information of the tap water to be used, and the information of the pH value of the kind of the disinfectant solution and the like are taken and stored into the memory 61 in the control section 52.

Note that acquisition of the hardness information of tap water is not by input from the operation panel 7 at the time of installation of the apparatus main body 2, but the hardness information of the tap water may be detected by the hardness sensor 50 provided in the apparatus main body 2, and the detected hardness information may be automatically stored in the memory 61 by control of the CPU 59.

Further, as for acquisition of the pH value that is the information of the kind of the disinfectant solution, for example, a pH sensor may be provided in the chemical tank 13 of the apparatus main body 2, the pH value of the disinfectant solution may be detected by the pH sensor, and the detected pH value may be automatically stored in the memory 61 by control of the CPU 59.

Figure 4:
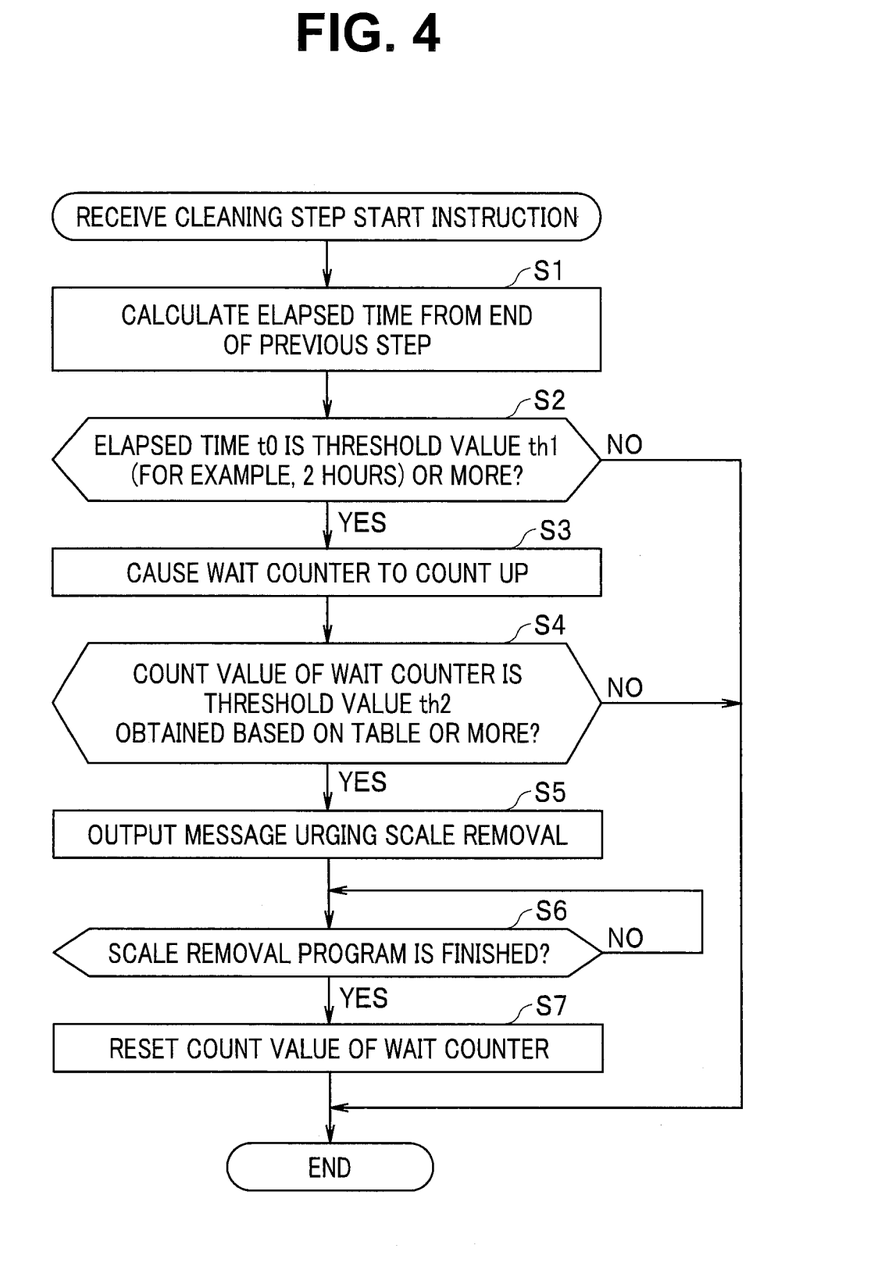
FIG. 4 is a flowchart showing a control example by a CPU shown in FIG. 3.

Next, an operation to be a feature of the endoscope cleaning/disinfecting apparatus of the present embodiment will be described with use of FIG. 4. FIG. 4 is a flowchart showing a control example by the CPU shown in FIG. 3.

In the endoscope cleaning/disinfecting apparatus 1 of the present embodiment, when execution of the cleaning and disinfecting step is instructed from the operation panel 7 of the apparatus main body 2, the CPU 59 of the control section 52 reads a determination program of scale removal shown in FIG. 4 from the ROM not illustrated and executes the determination program.

When the cleaning and disinfecting step of the endoscope cleaning/disinfecting apparatus 1 is started, the CPU 59 calculates an elapsed time t0 from end of the steps of cleaning, disinfecting and the like of the previous time, namely, a series of steps of the cleaning and disinfecting step and the dry step, based on the time information from the clock 60. Note that "RECEIVE CLEANING STEP START INSTRUCTION"

shown in FIG. 4 shows an instruction of start of execution of a series of steps of the cleaning and disinfecting step, and the dry step.

Thereafter, in processing of subsequent step S2, the CPU 59 determines whether or not the calculated elapsed time t0 is a threshold time th1 (here, for example, two hours) that is stored in the memory 61 or more. If the calculated elapsed time t0 is the threshold value time th1 or more in the determination process, the flow proceeds to step S3, and if the calculated elapsed time t0 is not the threshold value time th1 or more, the processing routine is ended.

In processing of step S3, the CPU 59 causes the wait counter that is not illustrated and is provided in the CPU 59 to count up, and updates the count value.

Note that the count value is a count value that is a result that states in which water does not flow after water is removed after the water is fed to the plurality of conduits 15, 16, 25 and the like of the endoscope cleaning/disinfecting section 1A are counted, and corresponds to the cleaning history information. In this case, the count value is the result of the states in which tap water does not flow into the plurality of conduits 15, 16 and 25 for a predetermined time period or more are counted, for example. The predetermined time period can be 1 second or more. As a setting method of the predetermined time period, the time period can be determined by being set at two hours, for example, with consideration given to easiness of precipitation of scale such as a dry situation of the installation area of the endoscope cleaning/disinfecting apparatus, and the hardness of tap water.

Namely, if two hours or more elapses after end of the series of steps of the cleaning and disinfecting step and the dry step, it is determined that an inside of the cleaning tank 8 and insides of the respective conduits 15, 16 and 25 are in a state in which scale easily adheres thereto due to residual water of the tap water after rinse. If the series of steps ends within a time period that does not reach two hours, it is determined that the inside of the cleaning tank 8 and the insides of the respective conduits 15, 16 and 25 are in a state in which scale is not formed even if residual water of tap water is present after rinse in the inside of the cleaning tank 8 and the insides of the respective conduits 15, 16 and 25. While the threshold value time th1 is desired to be set at two hours as a matter of course, the setting may be properly changed in accordance with necessity.

Figure 5:
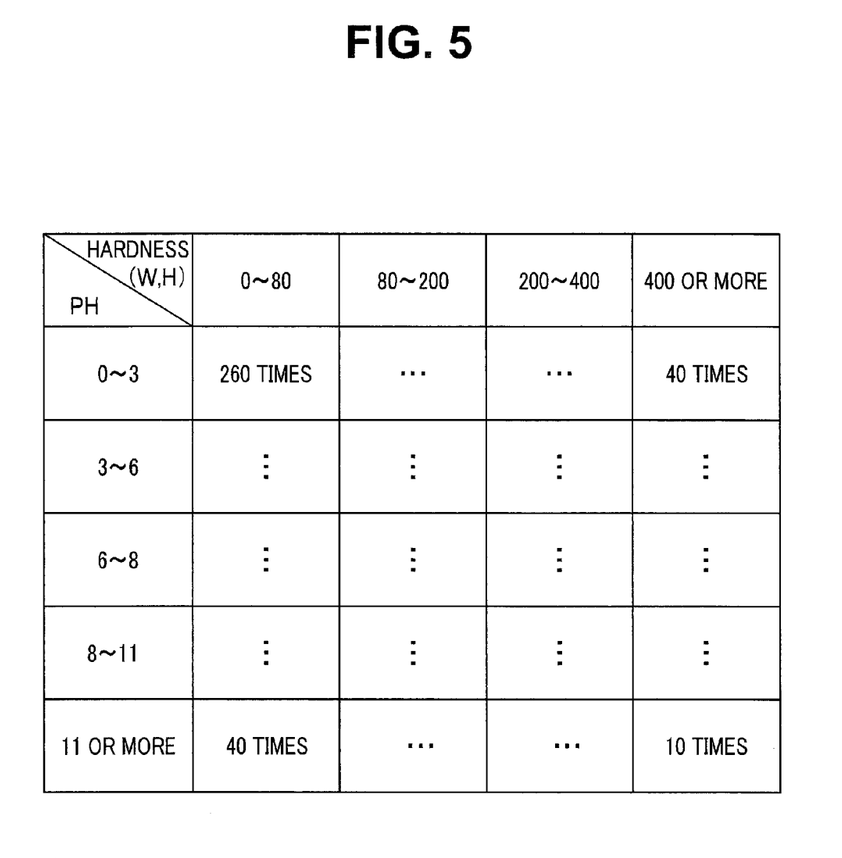
FIG. 5 is a diagram showing a table of pH-hardness and a count value, which is stored in a memory shown in FIG. 3.

Accordingly, the CPU 59 determines whether or not the count value of the wait counter, which is counted up in the processing of the step S3, is a threshold value th2 that is obtained based on the table shown in FIG. 5 or more by processing in subsequent step S4. Note that the threshold value th2 shows the number of times of execution of the series of steps of the cleaning and disinfecting step and the dry step.

For example, if the hardness information of the tap water which is stored in the memory 61 of the endoscope cleaning/disinfecting apparatus 1 in advance is high and "400 or more", and the pH value which is the information of the kind of the disinfectant solution is within the range of "0 to 3" and is a pH value with a high acidity concentration, the CPU 59 sets the number of times of execution of the steps which is the threshold th2 as "40".

Further, if the hardness information of the tap water which is stored in the memory 61 of the endoscope cleaning/disinfecting apparatus 1 in advance is high and "400", and the pH value which is the information of the kind of the disinfectant solution is "11 or more" and a pH value with a high alkalinity concentration, the CPU 59 sets the number of times of execution of the steps which is the threshold value th2 as "10".

Further, if the hardness information of the tap water stored in the memory 61 of the endoscope cleaning/disinfecting apparatus 1 in advance is within a range of "0 to 80" and is low conversely from the above description, and the pH value which is the information of the kind of the disinfectant solution is within a range of "0 to 3" and is a pH value with an extremely high acidity concentration, the CPU 59 sets the number of times of execution of the steps that is the threshold value th2 as "260".

Namely, as shown in FIG. 5, the threshold value th2 of the count value is set so that the number of times of execution of the steps which is the threshold value th2 becomes small so that scale removal is performed early, because as the hardness information of the tap water is higher, and the pH value of the disinfectant solution is a pH value with a higher alkalinity concentration, scale adheres more easily. In contrast therewith, the threshold value th2 of the count value is set so that the number of times of execution of the steps becomes large so that scale removal is performed later, because as the hardness information of the tap water is such that the tap water is soft water and has lower hardness, and the pH value of the disinfectant solution is a pH value with a higher acidity concentration, scale is less likely to adhere.

The CPU 59 proceeds to subsequent step S5, if the count value of the wait counter is the threshold value th2 which is obtained based on the table shown in FIG. 5 or more by the determination processing according to step S4, and the CPU 59 determines that scale removal is not necessary yet and ends the processing routine if the count value is not the threshold value th2 or more.

Figure 6:
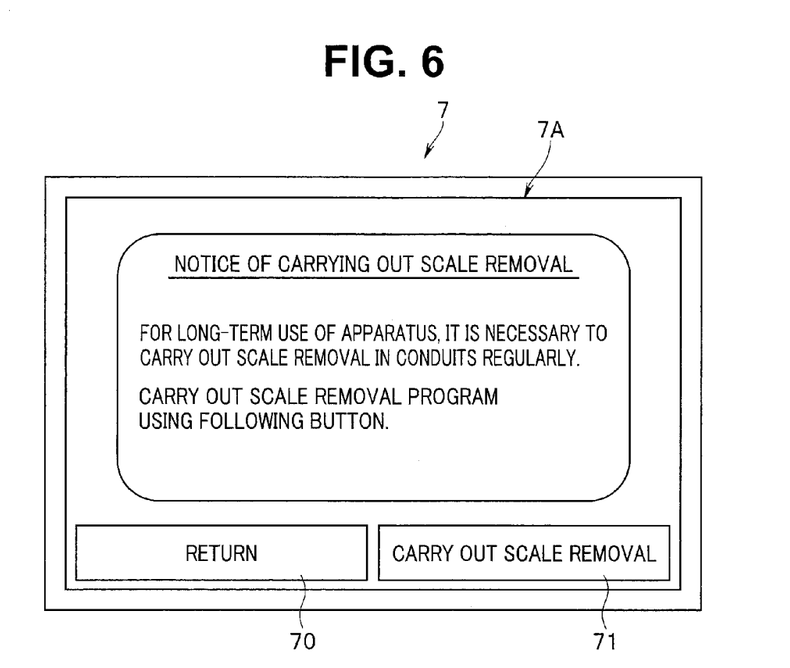
FIG. 6 is a diagram showing a display example for notifying notice of carrying out scale removal, which is displayed on an operation panel by processing of FIG. 4.

In processing of step S5, the CPU 59 outputs a message urging scale removal to the operation panel 7, for example. A display example of the message urging scale removal, which is displayed on the operation panel 7, is shown in FIG. 6. FIG. 6 is a diagram showing the display example for notifying notice of carrying out scale removal, which is displayed on the operation panel by the processing of step S5.

As shown in FIG. 6, the CPU 59 causes a scale removal carrying-out notification screen 7A, for example, to be displayed on the operation panel 7. On the scale removal carrying-out notification screen 7A, messages such as "NOTICE OF CARRYING OUT SCALE REMOVAL", "FOR LONG-TERM USE OF APPARATUS, IT IS NECESSARY TO CARRY OUT SCALE REMOVAL IN CONDUITS REGULARLY", and "CARRY OUT SCALE REMOVAL PROGRAM USING FOLLOWING BUTTON" are displayed. Further, at a lower portion of the scale removal carrying-out notification screen 7A, a button 70 to instruct "RETURN", and a button 71 to instruct "CARRY OUT SCALE REMOVAL" are displayed.

Note that while in the present embodiment, the message urging scale removal is outputted to the operation panel 7, whereby the scale removal carrying-out notification screen 7A is displayed on the operation panel 7, and the user is notified of the carrying out scale removal, the present invention is not limited thereto.

For example, the CPU 59 may provide notification by performing control to cause the printer section which is connected to the apparatus main body 2 to print out the message by outputting the message urging scale removal to the printer section, or to output a voice signal of the message urging scale removal to a speaker not illustrated and provided at the apparatus main body 2 to reproduce the message. Further, the CPU 59 may provide notification by performing control to cause a PC of the outside apparatus by using the RS 232C connection port 40, and an external device that is connected to the in-hospital network or the like by using the LAN connection port 41 to display the messages urging scale removal, or reproduce the message by voice.

Accordingly, by the processing routine as above, necessity or nonnecessity of removal of the scale that adheres to the cleaning tank 8, the conduits and the like can be automatically determined, at the same time as which, when scale removal is necessary, the message urging scale removal is displayed, and the user can be notified that scale removal is necessary.

Here, it is assumed that the user recognizes that carrying out scale removal is necessary, and executes the scale removal program, by the scale removal carrying-out notification screen 7A which is displayed on the operation panel 7. In this case, the user depresses the button 71 of "CARRY OUT SCALE REMOVAL" in the scale removal carrying-out notification screen 7A shown in FIG. 6.

Figure 7:
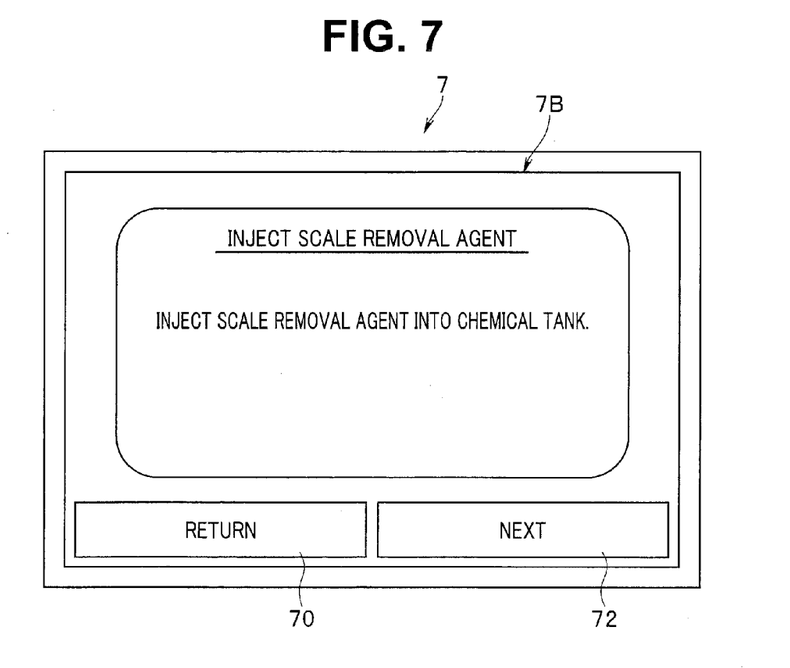
FIG. 7 is a diagram showing a display example for notifying an injection instruction of a scale removal agent when a scale removal carrying-out button on display of notice of carrying out scale removal of FIG. 6 is pressed down.

Thereupon, the CPU 59 causes a scale removal agent injection instruction screen 7B shown in FIG. 7 to be displayed on the operation panel 7. FIG. 7 is a diagram showing a display example for notifying an injection instruction of the scale removal agent when the scale removal carrying-out button on the scale removal carrying-out notification display of FIG. 6 is depressed.

On the scale removal agent injection instruction screen 7B shown in FIG. 7, messages such as "INJECT SCALE REMOVAL AGENT", and "INJECT SCALE REMOVAL AGENT INTO CHEMICAL TANK" are displayed. Further, at a lower portion of the scale removal agent injection instruction screen 7B, the button 70 to instruct "RETURN", and a button 72 to instruct "NEXT" are displayed.

The scale removal agent injection instruction screen 7B is displayed on the operation panel 7, for example, as above, whereby the user can be notified that the injection step of the scale removal agent is necessary.

When the user recognizes that scale removal agent injection is necessary by seeing the scale removal agent injection instruction screen 7B, the user injects the chemical solution 30a in the scale removal agent bottle 6x into the chemical tank 13 by tilting the scale removal agent bottle 6x in which the chemical solution 30a which is a scale removal agent is poured by hand, in the disinfectant solution bottle tray 6. Alternatively, when the user sets the scale removal agent bottle 6x in place of the disinfectant solution bottle 6a which is set to the disinfectant solution bottle tray 6, the chemical solution 30a is automatically injected into the chemical tank 13 via the conduit 31 by the pump 32 which configures the scale removal agent supply section by control of the CPU 59, instead of by hand.

Note that the scale removal agent is not limited to the chemical solution 30a such as a citric acid containing solution of a predetermined pH value as described above, and may be a liquid or a fluid including a solid with a high pH value and a high acidity concentration, or an abrasive.

Further, as another scale removal agent, a vapor-liquid two-phase flow (TPF) in which a gas and a liquid such as a chemical solution are mixed at a predetermined ratio is cited, for example. The liquid for use in the vapor-liquid two-phase flow is not specially limited, and, for example, use of a mixed solution generated from a plurality of kinds of chemical solutions is desirable.

When injection of the scale removal agent into the chemical tank 13 is completed as above, the user depresses the button 72 of "NEXT" in the scale removal agent injection instruction screen 7B shown in FIG. 7.

Figure 8:
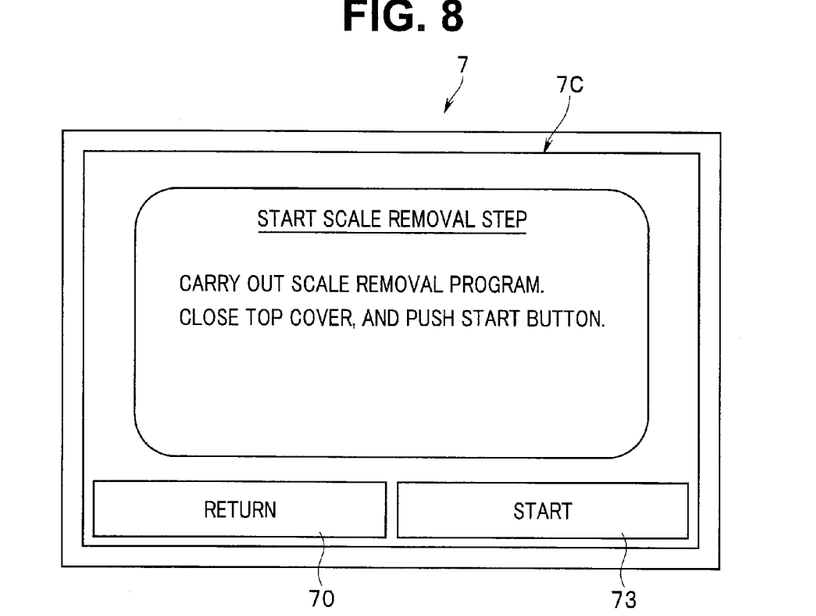
FIG. 8 is a diagram showing a display example for notifying a start instruction of a scale removal step after display of the scale removal agent injection instruction of FIG. 7 is displayed.

Thereupon, the CPU 59 causes a scale removal step start instruction screen 7C shown in FIG. 8 to be displayed on the operation panel 7. FIG. 8 is a diagram showing a display example for notifying a start instruction of the scale removal step after the scale removal agent injection instruction display of FIG. 7 is displayed.

On the scale removal step start instruction screen 7C shown in FIG. 8, messages such as "START SCALE REMOVAL STEP", and "CARRY OUT SCALE REMOVAL PROGRAM. CLOSE TOP COVER, AND PRESS START BUTTON" are displayed. Further, at a lower portion of the scale removal step start instruction screen 7C, the button 70 to instruct "RETURN", and a button 73 to instruct "START" are displayed.

The scale removal step start instruction screen 7C as above is displayed on the operation panel 7, for example, whereby the user can be notified that the start operation of the step of scale removal is necessary.

When the user recognizes that the start operation of the step of scale removal is necessary by the scale removal step start instruction screen 7C displayed on the operation panel 7, the user depresses the button 73 of "START" in the scale removal step start instruction screen 7C shown in FIG. 8.

Thereupon, the CPU 59 controls the electromagnetic valve 23 and the respective pumps 20 and 26 to supply the chemical solution 30a as the scale removal agent stored in the chemical tank 13 to the respective conduits 11, 19, 21 and 25 which are connected to the cleaning tank 8 of the endoscope cleaning/disinfecting section 1A and at the same time, the CPU 59 performs fluid control to circulate the chemical solution 30a between the chemical tank 13 and the cleaning tank 8, and between the circulation port 8b and the circulation nozzle 8c of the cleaning tank 8.

The chemical solution 30a as the scale removal agent is circulated between the cleaning tank 8 and the chemical tank 13, and between the circulation port 8b and the circulation nozzle 8c of the cleaning tank 8, whereby the scale that adheres to the inside of the cleaning tank 8 and the insides of the respective conduits 11, 19, 21 and 25 can be dissolved and removed.

Note that a circulating operation of the chemical solution 30a according to the scale removal step as above is performed for a set time period that is set in advance.

Figure 9:
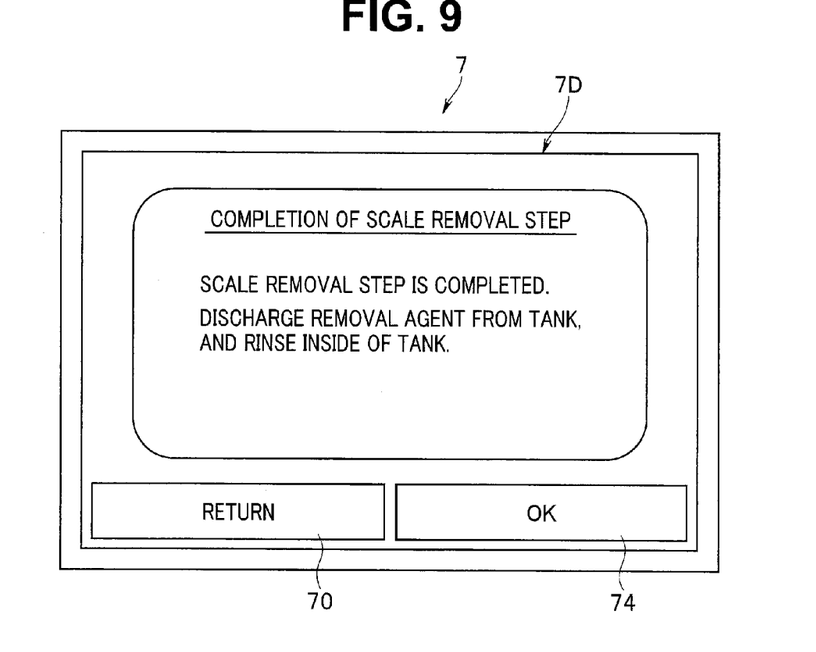
FIG. 9 is a diagram showing a display example for notifying completion of the scale removal step.

Subsequently, when the above described scale removal step is completed after the set time period, the CPU 59 recognizes the completion, and causes a scale removal step completion screen 7D shown in FIG. 9 to be displayed on the operation panel 7. FIG. 9 is a diagram showing a display example for notifying completion of the scale removal step.

On the scale removal step completion screen 7D shown in FIG. 9, messages such as "COMPLETION OF SCALE REMOVAL STEP", and "SCALE REMOVAL STEP IS COMPLETED. DISCHARGE REMOVAL AGENT FROM TANK, AND RINSE INSIDE OF TANK" are displayed. Further, at a lower portion of the scale removal step completion screen 7D, the button 70 to instruct "RETURN", and a button 74 to instruct "OK" are displayed.

The scale removal step completion screen 7D as above is displayed on the operation panel 7, for example, whereby the user can be notified that the step of scale removal is completed.

When the user recognizes that the step of scale removal is completed by the scale removal step completion screen 7D which is displayed on the operation panel 7, the user depresses the button 74 of "OK" in the scale removal step completion screen 7D shown in FIG. 9.

Thereupon, the CPU 59 controls the pumps 20 and 26 and feeds the chemical solution 30a that is stored in the chemical tank 13 and the conduit 25 to the cleaning tank 8 to store the chemical solution 30a in the cleaning tank 8, after which, the CPU 59 controls the electromagnetic valve 24 to discard the chemical solution 30a to the external exhaust port via the conduit 22.

Thereafter, the CPU 59 controls the respective electromagnetic valves 17, 18, 23 and 24, and the respective pumps 20 and 26 to take in the tap water, and performs control to rinse the inside of the cleaning tank 8, the inside of the chemical tank 13, and the insides of the respective conduits 11, 19, 21 and 25 by the tap water. Accordingly, the inside of the cleaning tank 8, the inside of the chemical tank 13 and the insides of the respective conduits 11, 19, 21, 22 and 25 are rinsed by the tap water, whereby the endoscope cleaning/disinfecting section 1A can be brought into a wait state for starting the next cleaning and disinfecting step.

Note that a rinse step by the tap water after discharge of the scale removal agent as above is performed for a set period of time that is set in advance.

Subsequently, when the CPU 59 completes the above described scale removal step after the set time period, the CPU 59 determines whether or not the scale removal program is completed according to the determination process of step S6 shown in FIG. 4.

In this case, when the CPU 59 determines that the scale removal program is completed based on the depressing operation on the "OK" button 64 on the scale removal step completion screen 7D shown in FIG. 9, for example, the CPU 59 proceeds to subsequent step S7, and when the CPU 59 determines that the scale removal program is not completed, the CPU 59 performs the determination processing of the step S6 until the scale removal program is completed.

Subsequently, in processing of step S7, the CPU 59 resets the count value of the wait counter not illustrated, and ends the processing routine.

As described above, according to the present embodiment, necessity or nonnecessity of removal of scale that adheres to the cleaning tank 8, the conduits 11, 19, 21 and 25 and the like can be automatically determined based on the hardness information of the tap water.

Further, when it is determined that removal of scale is necessary, the message urging scale removal can be outputted, and therefore, the user can be notified that removal of scale is necessary.

Furthermore, when the scale removal program is executed, fluid control can be performed so as to circulate the chemical solution 30a which is a scale removal agent into the endoscope cleaning/disinfecting section 1A, and therefore, scale can be easily removed.

Note that in the present embodiment, the configuration of the endoscope cleaning/disinfecting apparatus 1, which can automatically determine necessity or nonnecessity of removal of the scale that adheres to the cleaning tank 8, the conduits 11, 19, 21 and 25 and the like based on the hardness information of the tap water as described above, is described.

Furthermore, in the endoscope cleaning/disinfecting apparatus 1 of the present embodiment, the adhering state of scale also can be visually recognized and detected by the scale detecting bypass conduit 11 which is provided at the apparatus main body 2.

Figure 10:
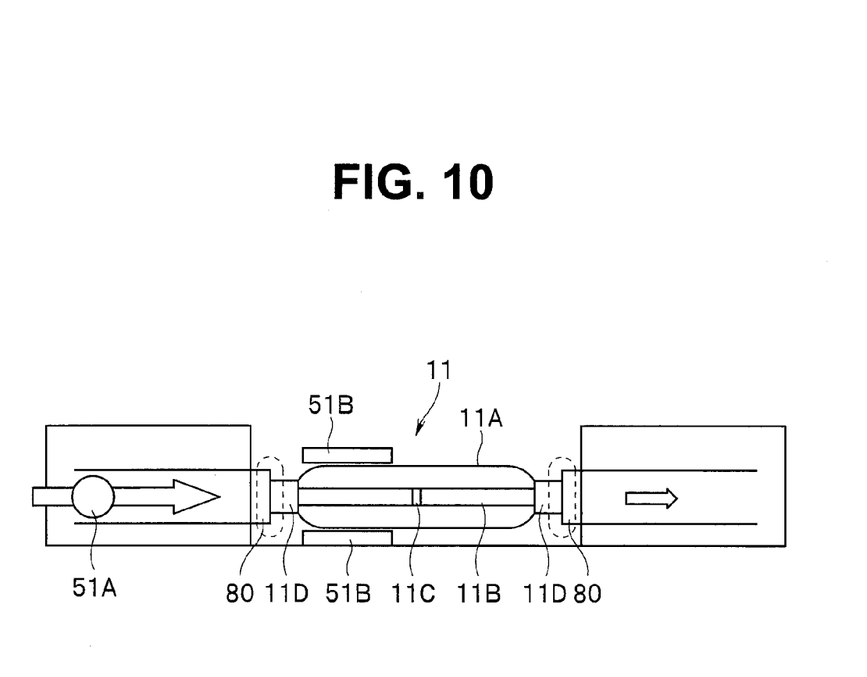
FIG. 10 is a configuration diagram showing a configuration example of a scale detecting bypass conduit that is provided at an apparatus main body of FIG. 1.

The scale detecting bypass conduit 11 is configured as shown in FIG. 10, for example. FIG. 10 is a configuration diagram showing a configuration example of the scale detecting bypass conduit that is provided at the apparatus main body of FIG. 1.

As shown in FIG. 10, the scale detecting bypass conduit 11 is configured by having, for example, a transparent cylindrical conduit member 11A, a bypass conduit member 11B that is inserted through an inside of the conduit member 11A, a filter 11C that is placed in an inside of a substantially center in a longitudinal direction of the bypass conduit member 11B, and connecting portions 11D that are disposed at both sides of the conduit member 11A and the bypass conduit member 11B.

The bypass conduit member 11B communicates with the conduit 25 (see FIG. 2) which is a circulation conduit in the apparatus main body 2. The filter 11C makes scale adhere thereto more easily than in an ordinary conduit. Further, the connecting portion 11D is a connecting member for making the conduit member 11A and the bypass conduit member 11B attachable and detachable to and from the conduit 25 in the apparatus main body 2.

Furthermore, in an inside at a liquid feeding side (a pump 26 side) for a liquid such as the diluted disinfectant solution 30, of the scale detecting bypass conduit 11, a flow sensor 51A (included in the other sensors 51) is provided. Further, at an outer periphery at the liquid feeding side (the pump 26 side) for the liquid, of the conduit member 11A, a pair of light transmission sensors 51B (included in the other sensors 51) are provided.

Accordingly, the scale detecting bypass conduit 11 of the configuration as above is provided, whereby the adhering state of scale in the conduit can be visually recognized and detected by the user similarly to the conduits of the endoscope cleaning/disinfecting section 1A. In this case, the filter 11C is provided, and thereby adherence of scale is quickened, whereby the timing at which removal of scale is necessary can be detected earlier than the timing at which the scale actually adheres to the inside of the cleaning tank and the insides of the conduits.

Further, the flow sensor 51A is provided, whereby if a change in the flow of the liquid detected by the flow sensor 51A is displayed on the operation panel 7 by control of the CPU 59, for example, whether or not scale adheres to the insides of the conduits can be monitored. In this case, if the flow of the liquid, which is detected by the flow sensor 51A is small, it can be determined that the insides of the conduits are in the state in which scale does not adhere to the inside of the conduits yet, whereas if the flow of the liquid detected by the flow sensor 51A is large conversely, it can be determined that the insides of the conduits are in the state in which scale adheres to the insides of the conduits, and it can be recognized that scale removal is necessary.

Further, the light transmission sensor 51B is provided, whereby if the result that is detected by the light transmission sensor 51B (a signal at a high level or a signal at a low level) is displayed on the operation panel 7 by control of the CPU 59, whether or not scale adheres to the insides of the conduits can be monitored.

In this case, if the detection result of the light transmission sensor 51B is a signal at a high level as a result that light is transmitted, it can be determined that the insides of the conduits are in the state in which scale does not adhere to the insides of the conduits yet, whereas if the detection result of the light transmission sensor 51B is a signal at a low level as a result that light is not transmitted conversely, it can be determined that the insides of the conduits are in the state in which scale adheres to the insides of the conduits, and it can be recognized that scale removal is necessary.

Accordingly, the scale detecting bypass conduit 11 as above is provided, whereby presence or absence of scale removal is visually recognized by the user without being automatically discriminated, and thereby presence or absence of removal of scale can be easily discriminated.

The present invention is not limited only to the embodiment described above, and can be carried out by being variously modified within the range without departing from the gist of the invention.

What is claimed is:

1. An endoscope cleaning/disinfecting apparatus, comprising:
   a cleaning tank in which an endoscope is disposed;
   a storage section that stores a chemical solution;
   a water supply connecting portion that is connectable to a water service pipe;
   an endoscope cleaning/disinfecting section having
   a first conduit that connects the cleaning tank and the storage section, and
   a second conduit that connects the cleaning tank and the water supply connecting portion;
   a water information input section to which hardness information of water that is supplied from the water service pipe is inputted;
   a history information retaining section that retains cleaning history information of the endoscope cleaning/disinfecting section; and
   a determination section that determines necessity or nonnecessity of scale removal of the endoscope cleaning/disinfecting section based on the hardness information and the cleaning history information.

2. The endoscope cleaning/disinfecting apparatus according to claim 1,
   wherein the cleaning history information is a count value that is obtained by counting a case in which a state where the first conduit does not contact the water continues for a predetermined time period or more after the first conduit contacts water and thereafter, the water is removed, as one time.

3. The endoscope cleaning/disinfecting apparatus according to claim 1, further comprising:
   a chemical solution information retaining section that retains a threshold value corresponding to information relating to a kind of a chemical solution that is stored in the storage section, and the hardness information,
   wherein the determination section determines necessity or nonnecessity of the scale removal based on whether or not the cleaning history information is not less than the threshold value.

4. The endoscope/cleaning disinfecting apparatus according to claim 1,
   wherein the storage section is capable of storing a scale removal agent,
   the apparatus further, comprising:
   a removal agent supply section that is connected to the storage section, and supplies the chemical solution or the scale removal agent to the endoscope cleaning/disinfecting section; and
   a control section that controls driving of the removal agent supply section based on the determination result.

5. The endoscope cleaning/disinfecting apparatus according to claim 4,
   wherein the control section controls the removal agent supply section to cause the scale removal agent to circulate in an inside of the endoscope cleaning/disinfecting section.

6. The endoscope cleaning/disinfecting apparatus according to claim 1,
   wherein the cleaning history information is a count value that is obtained by counting a case in which a state where the second conduit does not contact the water continues for a predetermined time period or more after the second conduit contacts water and thereafter, the water is removed, as one time.

* * * * *